United States Patent [19]

Suzuki et al.

[11] 4,081,334
[45] Mar. 28, 1978

[54] ANTIGEN MEMBRANES FOR USE IN SYPHILIS DIAGNOSIS AND SYPHILIS DIAGNOSIS APPARATUS USING SUCH MEMBRANES

[75] Inventors: Shuichi Suzuki; Masuo Aizawa, both of Tokyo; Isao Ishigur, Kasugai; Rikio Shinohara, Kagamihara; Yoichi Nagamura, Toyoake, all of Japan

[73] Assignee: Nippon Chemiphar Co., Ltd., Tokyo, Japan

[21] Appl. No.: 779,139

[22] Filed: Mar. 18, 1977

[30] Foreign Application Priority Data

| Mar. 18, 1976 | Japan | 51-29632 |
| Mar. 18, 1976 | Japan | 51-29633 |
| Mar. 18, 1976 | Japan | 51-29634 |
| Jun. 21, 1976 | Japan | 51-81408 |

[51] Int. Cl.² .......................... G01N 27/46
[52] U.S. Cl. .................. 204/1 T; 204/195 M; 204/195 B; 204/296
[58] Field of Search ............... 204/195 M, 1 T, 296, 204/195 B, 1 E; 128/2 E, 2.1 E; 324/29

[56] References Cited

PUBLICATIONS

Richard A. Durst, "Ion–Selective Electrodes", N.B.S. Spec. Pub. 314, (1969).

*Primary Examiner*—G. L. Kaplan
*Attorney, Agent, or Firm*—Oblon, Fisher, Spivak, McClelland & Maier

[57] ABSTRACT

An antigen membrane for syphilis diagnosis comprises cardiolipin immobilized in a polymer maxtrix. The membranes are used in syphilis diagnosis and in an apparatus for syphilis diagnosis.

17 Claims, 7 Drawing Figures

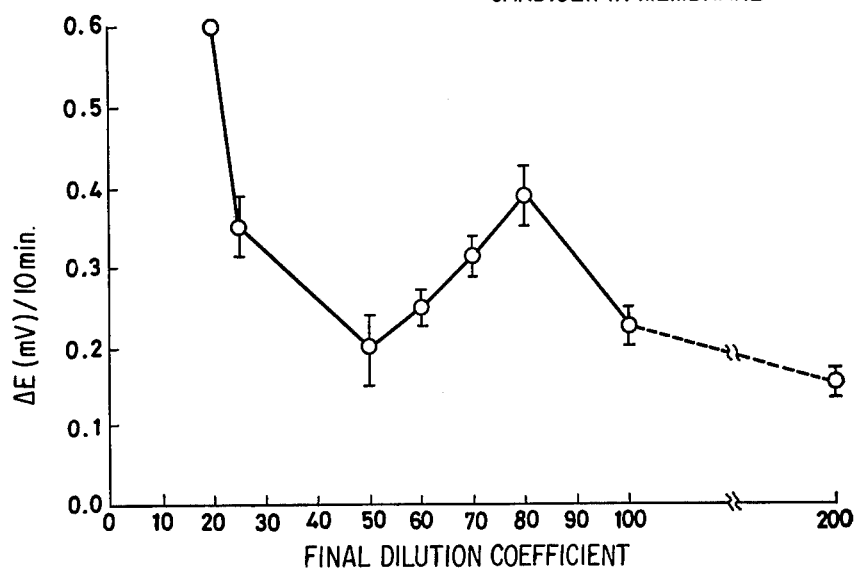
FIG. 6 EFFECT OF SERUM DILUTION ON MEMBRANE POTENTIAL AT LOW CONCENTRATION CARDIOLIPIN MEMBRANE
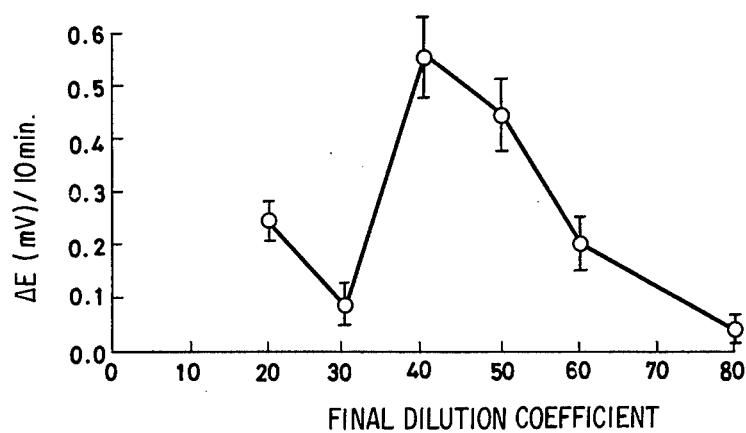
FIG. 7 EFFECT OF SERUM DILUTION ON MEMBRANE POTENTIAL AT HIGH CONCENTRATION CARDIOLIPIN MEMBRANE

ANTIGEN MEMBRANES FOR USE IN SYPHILIS DIAGNOSIS AND SYPHILIS DIAGNOSIS APPARATUS USING SUCH MEMBRANES

BACKGROUND OF THE INVENTION

1. Field of the Invention

This invention relates to an antigen membrane for syphilis diagnosis, and a method and apparatus for syphilis diagnosis.

2. Description of the Prior Art

Recently, with rapid progress in the field of immunology, important applications of immunology, have been developed, in particular, the introduction of immunochemical methods into clinical analysis, where their usefulness has been confirmed. In most immunoassays, the superior specificity of antigen-antibody reactions is utilized, and a trace amount of a specific substance can be selectively detected.

Syphilis diagnosis is a typical example of the application of such immuno-chemical clinical analyses. However, in the conventional syphilis diagnosis method, completion of the antigen-antibody complex forming reaction is observed with the naked eye. Accordingly, the excellent selectivity and sensitivity of the immuno-chemical specificity are not sufficiently utilized in the final diagnosis step.

Recently, a technical method has been developed by which biologically active compounds, such as enzymes are immobilized in insoluble matrices without losing their function, thus rendering these compounds available for use in the solid state.

SUMMARY OF THE INVENTION

In consideration of the above described facts, one object of this invention is to provide an insoluble polymer material to which is attached an antigen, whereby syphilis antibodies of a syphilitic patient can be exactly and reproducibly detected, that is, to provide an immobilized antigen membrane for syphilis diagnosis.

Another object of this invention is to provide a method for a syphilis diagnosis using the immobilized antigen membrane.

A further object of this invention is to provide syphilis diagnosis.

According to this invention, the above objects are attained by immobilizing cardiolipin in a polymer matrix.

DETAILED DESCRIPTION OF THE PREFERRED EMBODIMENT

One milliliter of Ogata antigen, which consists of 0.01% cardiolipin, 0.04% lecithin, 0.20% cholesterin in ethanol and which is used in the Wasserman test for syphilis, is mixed with 6 milliliters of an acetone solution containing 250 milligrams of acetyl cellulose. The mixed solution is cast on a glass plate (18 × 10 cm$^2$), and dried at room temperature under reduced pressure, after which the cast membrane is peeled off the glass plate. Thus, an immobilized antigen membrane is obtained.

Several methods such as covalent binding, entrapment, and adsorption can be used for immobilizing antigen while retaining its activity. Advantageously, when the entrapment method is employed, little lowering of the activity is observed.

Cellulose derivatives such as triacetyl cellulose and cellulose acetate as well as different natural or synthetic polymers can be used for membrane matrices.

According to this invention, any one of the following three diagnosis methods can be used.

The first diagnosis method is characterized in that one surface of the antigen membrane for syphilis diagnosis contacts the solution to be tested, and the other surface of the antigen membrane for syphilis diagnosis contacts normal blood serum, whereby the membrane potential of the antigen membrane is electrochemically measured to detect the syphilis antibodies.

The second diagnosis method is characterized in that the antigen membrane for syphilis diagnosis and an antigen-free membrane are piled one on another, and the solution to be tested contacts both surfaces of the piled membrane, whereby the membranes potential of the piled membrane is electrochemically measured to detect the syphilis antibodies.

The third diagnosis method is characterized in that one surface each of the antigen membrane for syphilis diagnosis and the antigen-free membrane contacts the solution to be tested, and the other surface of the antigen membrane for syphilis diagnosis and the antigen-free membrane contacts electrolyte, whereby the membrane potential of the antigen membrane for syphilis diagnosis is electrochemically measured to detect the syphilis antibodies.

The antigen-free membrane can be a polymer membrane containing non-Ogata antigen. For example, the antigen-free membrane can be prepared in such a manner that 6 milliliters of acetone solution containing 250 milligrams of acetyl cellulose is cast on a glass plate (18 × 10 cm$^2$) and dried at room temperature under reduced pressure, after which the cast membrane is peeled off the glass plate.

According to this invention, any one of four types of apparatus to be described in detail hereinafter with reference to the drawings can be used. The above described diagnosis methods will also be described in detail below.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein:

FIG. 6 shows the effect of serum dilution on membrane potential on a low concentration cardiolipin membrane.

FIG. 7 shows the effect of serum dilution on membrane potential on a high concentration cardiolipin membrane.

Referring to FIG. 2, an electrolytic cell 1 is partitioned into two compartments 3, 4 by a vertical wall 2. One compartment 3 partitioned by the wall is filled with a solution to be tested, while the other compartment 4 is filled with normal blood serum. An opening 2a made at the center of the vertical wall 2 is closed by an immobilized antigen membrane 5. Electrodes 6 and 7, which for example, may be made of calomel or Ag—AgCl, are disposed in the compartment 3 filled with the solution to be tested and in the other compartment 4 filled with the normal blood serum, respectively. The electrodes 6 and 7 are connected to input terminals of an amplifier 8 and an output terminal of the amplifier 8 is connected to a detector 9 for measuring the potential difference across the immobilized antigen membrane.

Figure 1:
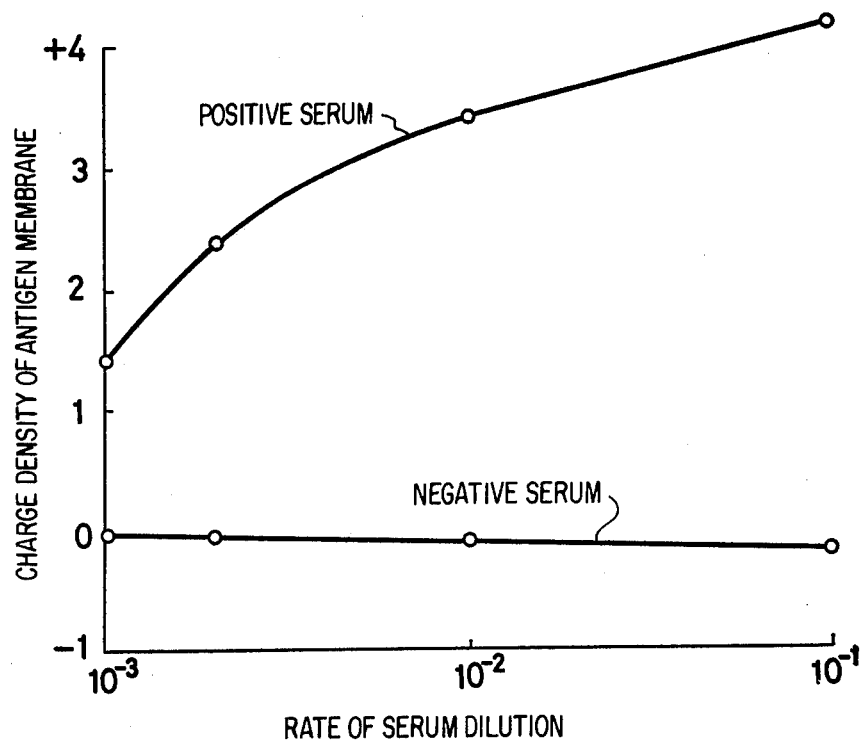
FIG. 1 shows a plot of the charge density of the antigen membrane vs. the rate of serum dilution for the experiment in part 2 of the example.
Figure 2:
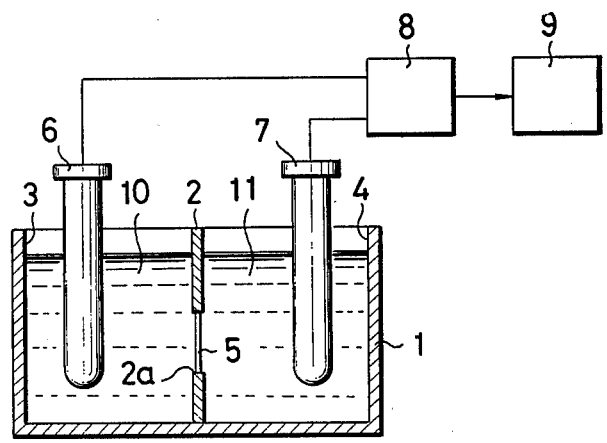
FIG. 2 shows a schematic cross-sectional view of a syphilis diagnosis apparatus used for the first syphilis diagnosis method.

In the syphilis diagnosis, a requisite amount of serum solution 10 to be tested, diluted with physiological saline, is poured into the compartment 3, while a requisite amount of normal serum solution 11, diluted with physiological saline, is poured into the compartment 4. When the serum concentrations of the solutions 10 and 11 are substantially equal to each other, and no syphilis antibodies are present in the solution 10 to be tested, the charge density is substantially the same at both sides of the immobilized antigen membrane, and so the membrane potential is nearly zero.

When syphilis antibodies are present in the serum solution 10 to be tested, the antibodies react with the antigen exposed on the surface of the antigen membrane 5 in contact with the serum solution 10. An antigen-antibody complex is formed on the surface of the membrane 5. The membrane 5 becomes an asymmetric membrane. Accordingly, the one surface of the antigen membrane 5 in contact with the normal serum solution 11 is electrically charged due to the property of the antigen membrane 5 itself, while the other surface of the antigen membrane 5 in contact with the serum solution 10 to be tested is electrically charged due to the property of the antigen-antibody complex. The charge-densities of the two surfaces are different from each other. Th difference of the charge densities is most detectably exhibited as a membrane potential. Accordingly, the antigen-antibody reaction is followed by measuring the membrane potential. The membrane potential is electrochemically led to the amplifier 8 through the electrodes 6 and 7, and amplified thereby. The output of the amplifier 8 is applied to the detector 9. The presence of the syphilis antibodies is detected using the output of the detecter 9. The membrane potential $\Delta\Psi$ is expressed by the following equation:

$$\Delta\phi = \frac{RT}{F} \ln \frac{\theta_2 + (\theta_2^2 + \Delta C^2)^{\frac{1}{2}}}{\theta_1 + (\theta_1 + \Delta C^2)^{\frac{1}{2}}}$$

where $\theta_1$ represents the charge density of one surface of the antigen membrane in contact with the normal serum solution; $\theta_2$, the charge density of the other surface of the antigen membrane on which the antigen-antibody complex is formed, and which contacts the serum solution to be tested; $c$, the concentration of the electrolyte; R, the gas constant; T, the absolute temperature (° K); and F, the Faraday constant.

Figure 3:
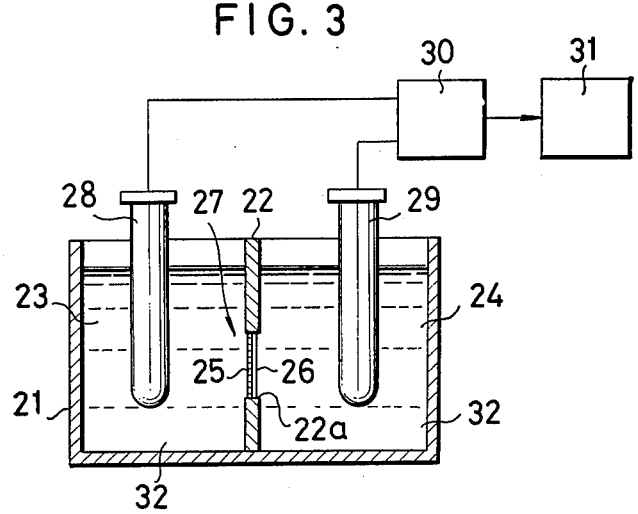
FIG. 3 shows a schematic cross-sectional view of a syphilis diagnosis apparatus used for the second syphilis diagnosis method.

Referring to FIG. 3, an electrolytic cell 21 is partitioned into two parts by a vertical wall 22. Both parts, namely compartments 23 and 24, are filled with the solution to be tested. An opening 22a made at the center of the vertical wall 22 is closed by a piled membrane body 27 of an immobilized antigen membrane 25 and an antigen-free membrane 26. Electrodes 28 and 29, which for example, may be made of calomel or Ag—AgCl, are disposed in the compartments 23 and 24 filled with the solution to be tested, respectively. The electrodes 28 and 29 are connected to input terminals of an amplifier 30, and an output terminal of the amplifier 30 is connected to a detector 31 for measuring the membrane potential of the piled membrane body 27.

In the syphilis diagnosis, a requisite amount of blood serum solution 32 to be tested, diluted with physiological saline, is poured into the compartments 23 and 24. When no syphilis antibody exists in the serum solution to be tested, no antigen-antibody reaction occurs on the surface of the antigen membrane 25 in contact with the serum solution. The charge density is substantially the same on both surfaces of the piled membrane body 27, and so the membrane potential is nearly zero.

When syphilis antibodies are present in the serum solution 32 to be tested, the antibodies react with the antigen exposed on the surface of the antigen membrane 25 in contact with the serum solution 32. An antigen-antibody complex is formed on one surface of the piled membrane body 27. The piled membrane 27 becomes asymmetric. Accordingly, the surface of the antigen-free membrane 26 of the piled membrane body 27 in contact with the serum solution 32 to be tested is electrically charged due to the property of the antigen-free membrane 26 itself, while the surface of the antigen membrane 25 of the piled membrane body 27 in contact with the serum solution 32 to be tested is electrically charged due to the properties of the antigen-antibody complex. The charge-densities of the two surfaces of the piled membrane body 27 are different from each other. The difference of the charge densities is detectably exhibited as a membrane potential. Accordingly, the antigen-antibody reaction is followed by measuring the membrane potential. The membrane potential is electrochemically led through the electrodes 28 and 29 to the amplifier 30, and amplified thereby. The output of the amplifier 30 is applied to the detector 31. The presence of the syphilis antibodies are detected using the output of the detecter 31. The membrane potential $\Delta\Psi$ is expressed by the following equation:

$$\Delta\phi = \frac{RT}{F} \ln \frac{\theta_2 + (\theta_2^2 + \Delta C^2)^{\frac{1}{2}}}{\theta_2 + (\theta_1^2 + \Delta C^2)^{\frac{1}{2}}}$$

where $\theta_1$ represents the charge density of the surface of the antigen-free membrane in contact with the serum solution 32 to be tested; $\theta_2$, the charge density of the surface of the antigen membrane on which the antigen-antibody complex is formed, and which contacts the serum solution 32 to be tested; C, the concentration of the electrolyte; R, the gas constant; T, the absolute temperature (° K), and F, the Faraday constant.

Figure 4:
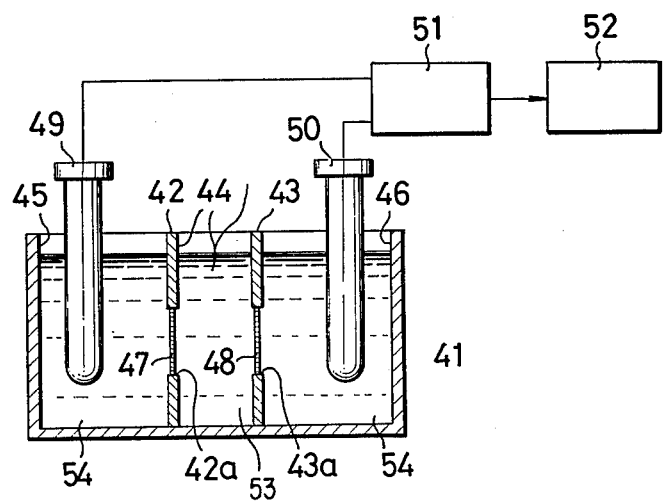
FIG. 4 shows a schemtatic cross-sectional view of a syphilis diagnosis apparatus used for the third syphilis diagnosis method.

Referring to FIG. 4, an electrolytic cell 41 is partitioned into three parts by vertical walls 42 and 43. The central compartment 44 is filled with the solution 53 to be tested. The left and right compartments 45 and 46 are filled with the electrolyte 54. Openings 47 and 48 made on the vertical walls 42 and 43 are closed by an immobilized antigen membrane 47 and an antigen-free membrane 48. Electrodes 49 and 50, which for example, may be made of calomel or Ag—AgCl, are disposed in the left and right compartments 45 and 46. The electrodes 49 and 50 are connected to input terminals of an amplifier 51, and an output terminal of the amplifier 51 is connected to a detector 52 for measuring the membrane potential of the immobilized antigen membrane.

In the syphilis diagnosis, a requisite amount of physiological saline containing anti-serum is poured into the compartment 44, while a requisite amount of physiological saline is poured into the compartments 45 and 46. When syphilis antibodies are present in the serum solution 53, the antibodies react with the antigen exposed on the surface of the immobilized antigen membrane 47 in contact with the physiological saline 53 containing the anti-serum. The antigen-antibody complex is formed on the surface of the antigen membrane 47. The antigen membrane 47 becomes asymmetric. Accordingly, the one surface of the antigen membrane 47 in contact with the physiological saline 54 is electrically charged due to the property of the antigen membrane itself, while the other surface of the antigen membrane 47 in contact with the physiological saline 53 containing the anti-serum is electrically charged due to the property of the antigen-antibody complex. The charge densities of the two surfaces are different from each other. The difference of the charge densities is detectably exhibited as a membrane potential. The antigen-antibody reaction is followed by the measurement of the membrane potential. The membrane potential is led to the amplifier 51 through the electrodes 49 and 50, and amplified thereby. The output of the amplifier 51 is applied to the detector 52. The presence of the syphilis antibodies are detected using the output of the detector 52. The membrane potential $\Delta\Psi$ is expressed by the following equation:

$$\Delta\phi = \frac{RT}{F} \ln \frac{\theta_2 + (\theta_2^2 + \Delta C^2)^{\frac{1}{2}}}{\theta_2 + (\theta_1^2 + \Delta C^2)^{\frac{1}{2}}}$$

where $\theta_1$ represents the charge density of the surface of the antigen membrane in contact with the physiological saline, $\theta_2$, the charge density of the surface of the antigen membrane on which the antigen-antibody complex is formed; C, the concentration of the electrolyte; R, the gas constant; T, the absolute temperature (° K); and F, the Faraday constant.

When the concentration of the electrolyte, for example, physiological saline, contained in the compartment 44, is equal to the concentration of the electrolyte contained in the compartments 45 and 46, the membrane potential of the antigen membrane is zero. No antigen-antibody reaction occurs on the antigen-free membrane 48.

The reason that the electrodes 49 and 50 are separated from the solution to be tested is that insulating films are otherwise formed on the electrodes 49 and 50 in contact with protein solution such as an anti-serum containing solution, due to an electrolytic phenomenon, causing errors in the measurement of the membrane potential, and resulting in poor reproducibility and tedious cleaning of the electrodes 49 and 50.

Figure 5:
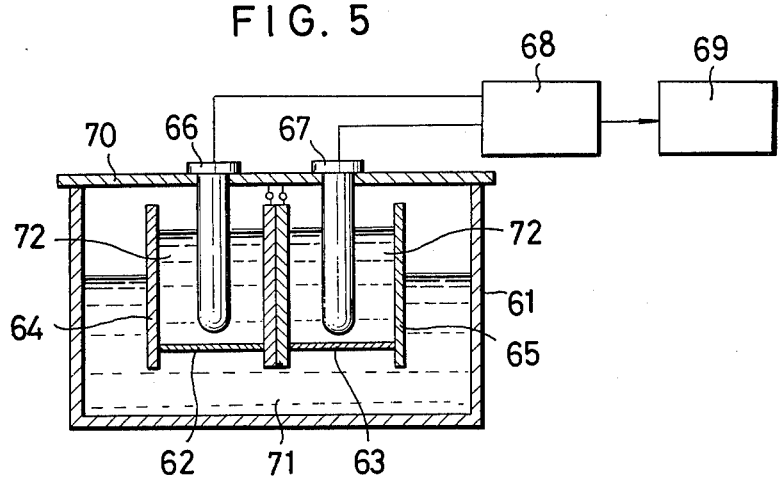
FIG. 5 shows a schematic cross-sectional view of a syphilis diagnosis apparatus used for the third syphilis diagnosis method, similar to FIG. 4.

Referring to FIG. 5, smaller cells 64 and 65 filled with the electrolyte are disposed in a larger cell 61 filled with the solution to be tested. An immobilized antigen membrane 62 and an antigen-free membrane 63 are stretched at the bottoms of the smaller cells 64 and 65, respectively. The lower surface of the immobilized antigen membrane 62 and that of the antigen-free membrane 63 are in contact with the solution 71 to be tested and contained in the larger cell 61. Electrodes 66 and 67, which for example, may be made of calomel or Ag—AgCl, are disposed in the cells 64 and 65, respectively. The electrodes 66 and 67 are connected to input terminals of an amplifier 68, and an output terminal of the amplifier 68 is connected to a detector 69 for measuring the membrane potential of the immobilized antigen membrane.

The smaller cells 64 and 65 may be separated from each other, or they may be integral with each other along one side wall. The immobilized antigen membrane 62 and the antigen-free membrane 63 are preferably attached at a higher point than the lower ends of the smaller cells 64 and 65 in order to prevent breaking the membranes 62 and 63.

The smaller cells 64 and 65 need only to be arranged so that the lower surfaces of the immobilized antigen membrane 62 and the antigen-free membrane 63 are in contact with the solution 71 to be tested. For example, a bar 70 may be fitted to the opening of the larger cell 61 to hold the electrodes 66 and 67, and to hold demountably the smaller cells 64 and 65. That is very convenient for the exchange operation of the cells 64 and 65 after use. The lower ends of the cells 64 and 65 should not be in contact with the bottom of the larger cell 61. However, legs extending to the bottom of the larger cell 61 may be attached to the lower ends of the smaller cells 64 and 65.

In the syphilis diagnosis, a requisite amount of physiological saline 71 containing the blood serum solution to be tested is poured into the cell 61, while a requisite amount of physiological saline 72 is poured into the cells 64 and 65. The antibodies react with the antigen exposed on the surface of the immobilized antigen membrane 62 in contact with the physiological saline 71 containing the anti-serum. An antigen-antibody complex is formed on the surface of the antigen membrane 62. The antigen membrane 62 becomes asymmetric. The one surface of the antigen membrane 62 in contact with the physiological saline 72 is electrically charged due to the property of the membrane itself, while the other surface of the antigen membrane 62 in contact with the physiological saline 71 containing the anti-serum is electrically charged due to the property of the antigen-antibody complex. There is some difference of the charge density between the upper and lower surfaces. The difference of the charge densities is detectably exhibited as a membrane potential. Accordingly, the antigen-antibody reaction is followed by the measurement of the membrane potential. The membrane potential is led to the amplifier 68 through the electrodes 66 and 67, and amplified thereby. The output of the amplifier 68 is applied to the detector 69. The presence of the syphilis antibodies is detected using the output of the detector 69. The membrane potential $\Delta\Psi$ is expressed by the following equaiton;

$$\Delta\phi = \frac{RT}{F} \ln \frac{\theta_2 (\theta_2^2 + \Delta C^2)^{\frac{1}{2}}}{\theta_1 + (\theta_1^2 + \Delta C^2)^{\frac{1}{2}}}$$

where $\theta_1$ represents the charge density of the surface of the antigen membrane in contact with the physiological saline; $\theta_2$, the charge density of the surface of the antigen membrane on which the antigen-antibody complex is formed; C, the concentration of the electrolyte; R, the gas constant; T, the absolute temperature (° K); and F, the Faraday constant.

When the concentration of the electrolyte, for example, physiological saline, contained in the cell 61, is equal to the concentration of the electrolyte contained in the cells 64 and 65, the membrane potential of the antigen membrane is zero. No antigen-antibody reaction occurs on the antigen-free membrane 63.

The reason that the electrodes 66 and 67 are separated from the solution to be tested is that insulating films are otherwise formed on the electrodes 66 and 67 in contact with a protein solution such as a solution containing anti-serum, due to an electrolytic phenomenon, causing errors in the measurement of the membrane potential, resulting in poor reproducibility and requiring that the electrodes 66 and 67 be cleaned.

According to this invention, as described above, antigen capable of reacting with a substance to be detected is immobilized in a membrane, and the target substance, namely syphilis antibody, can be selectively and directly detected by measuring the membrane potential of the immobilized antigen membrane. In contrast to the conventional diagnosis using the naked eye, the final decision is made on the basis of an electric signal derived from the membrane potential. Accordingly, any error in the reading is very small, and there is little difference between diagnoses carried out by different persons. The separation of the antigen-antibody complex is not required. The diagnosis operation is very simple. The syphilis diagnosis is exact and reproducible.

Next, one example will be described.

EXAMPLE (1) Preparation of the immobilized antigen membrane.

Acetyl cellulose (acetyl value 38%; manufactured by Wako Junyaku Co., Ltd.) and Ogata antigen (manufactured by Sumitomo Chemical Industrial Co., Ltd., for the Wasserman syphilis test reaction; consisting of 0.01% cardiolipin, 0.04% lecithin, 0.20% cholesterin in ethanol) were used to prepare an immobilized antigen membrane.

One milliliter of the above described Ogata antigen was mixed with 6 milliliters of acetone solution containing 250 milligrams of acetyl cellulose. The mixed solution was cast on a glass plate (18 × 10 cm$^2$) and dried at room temperature under reduced pressure. After dried, after which the film was peeled from the glass plate. Thus, an immobilized antigen membrane was obtained.

An acetone solution of acetyl cellulose was used to prepare an acetyl cellulose membrane containing no antigen in the above described manner.

(2) Diagnosis experiment on syphilis serum.

(A) Physiological saline was used as electrolyte. Positive serology control serum for syphilis diagnosis (manufactured by DADE) diluted to $10^{-3}$, $10^{-2}$ and $10^{-1}$ was used as the solutions to be tested. Membrane potentials were measured for the respective control serum solutions.

The results are shown in FIG. 1.

The positive serology control serum exhibits a weak potential at a dilution of 1/16 by the VDRL method, and at a dilution of 1/32 by the RPR and USR methods.

(B) The comparison of the present method (ICES) and conventional methods (VDRL, TPHA and Ogata Method) is shown in Table 1. Samples 1 to 11 are patients' sera.

Table 1

| Sample | VDRL | TPHA | Ogata | Method | ICES(mV) |
|---|---|---|---|---|---|
| 1 | − | − | − |  | −0.01 |
| 2 | + | + | × | 2 | 0.03 |
| 3 | + | + | × | 2 | 0.05 |
| 4 | + | + | × | 4 | 0.08 |
| 5 | + | + | × | 4 | 0.07 |
| 6 | + | + | × | 16 | 0.10 |
| 7 | + | + | × | 16 | 0.11 |
| 8 | + | + | × | 32 | 0.15 |
| 9 | + | + | × | 32 | 0.17 |
| 10 | + | + | × | 320 | 0.17 |
| 11 | + | + | × | 320 | 0.14 |

What is claimed is:

1. An antigen membrane for syphilis diagnosis comprising cardiolipin immobilized on a polymer matrix.

2. The antigen membrane for syphilis diagnosis of claim 1, in which said polymer is a cellulose derivative.

3. A method for diagnosing syphilis, comprising bringing one surface of the antigen membrane of claim 1 into contact with a solution to be tested; bringing the other surface of said antigen membrane into contact with a normal serum solution; and measuring electrochemically the membrane potential generated across said antigen membrane.

4. A method for diagnosing syphilis comprising piling the antigen membrane of claim 1 and an antigen-free membrane to form a piled membrane body; bringing both surfaces of said piled membrane body into contact with a solution to be tested; and measuring electrochemically the membrane potential generated across said piled membrane body.

5. The method of claim 4, in which said antigen-free membrane is a polymer membrane containing no cardiolipin.

6. The method of claim 5, in which said polymer is a cellulose derivative.

7. A method for diagnosing syphilis, comprising bringing one surface of the antigen membrane of claim 1 and one surface of an antigen-free membrane into contact with a solution to be tested; bringing the other surface of said antigen membrane and said antigen-free membrane into contact with an electrolyte; and measuring the membrane potential generated across said antigen membrane.

8. The method claim 7, in which said electrolyte is physiological saline.

9. The method of claim 7, in which said antigen-free membrane is a polymer membrane containing no cardiolipin.

10. An apparatus for use in diagnosing syphilis comprising an electrolytic cell partitioned into two compartments by the antigen membrane of claim 1; electrodes disposed in said compartments; and a detector connected to said electrodes for measuring the membrane potential across said antigen membrane.

11. An apparatus for use in diagnosing syphilis comprising, an electrolytic cell partitioned into two compartments by the piled membrane body of claim 4; electrodes disposed in said two compartments; and a detector connected to said electrodes for measuring the membrane potential of said piled membrane body.

12. The apparatus of claim 11 in which said antigen-free membrane is a polymer matrix membrane containing no cardiolipin.

13. The apparatus of claim 12, in which said polymer matrix is a cellulose derivative.

14. An apparatus for use in diagnosing syphilis comprising an electrolytic cell partitioned into three compartments by the antigen membrane of claim 1, and by an antigen-free membrane, electrodes disposed in the two outer said compartments; and a detector connected to said electrodes for measuring the membrane potential of said antigen membrane.

15. The apparatus of claim 14, wherein the central one of said three compartments is adapted to be filled with the solution to be tested and the outer two compartments are filled with an electrolyte.

16. An apparatus for diagnosing syphilis comprising a first electrolytic cell; a second pair of electrolytic cells disposed inside said first electrolytic cell; the antigen membrane of claim 1 being stretched across the bottom of one of said second pair of electrolytic cells, and an antigen-free membrane being stretched across the bottom of the other of said cells; an electrode disposed in each of said second pair of electrolytic cells; and a detector connected to said electrodes for measuring the membrane potential of said antigen membrane.

17. The apparatus of claim 16, wherein said inner cells contain electrolyte and said first cell is adapted to contain the solution to be tested.

* * * * *